United States Patent
Paré et al.

(10) Patent No.: US 9,146,346 B2
(45) Date of Patent: Sep. 29, 2015

(54) OPTICAL FIBER FOR COHERENT ANTI-STOKES RAMAN SCATTERING ENDOSCOPES

(71) Applicant: INSTITUT NATIONAL D'OPTIQUE, Québec (CA)

(72) Inventors: Claude Paré, Saint-Augustin-de-Desmaures (CA); Huimin Zheng, Québec (CA); Pascal Deladurantaye, Saint-Joseph-de-la-Pointe-de-Lévis (CA); Jean-François Cormier, Saint-Augustin-de-Desmaures (CA)

(73) Assignee: INSTITUT NATIONAL D'OPTIQUE, Québec, Quebec (CA)

( * ) Notice: Subject to any disclaimer, the term of this patent is extended or adjusted under 35 U.S.C. 154(b) by 148 days.

(21) Appl. No.: 14/169,889

(22) Filed: Jan. 31, 2014

(65) Prior Publication Data

US 2014/0212083 A1    Jul. 31, 2014

Related U.S. Application Data

(60) Provisional application No. 61/758,852, filed on Jan. 31, 2013.

(51) Int. Cl.
*G02B 6/24* (2006.01)
*G02B 6/024* (2006.01)
(Continued)

(52) U.S. Cl.
CPC ............ *G02B 6/024* (2013.01); *G02B 6/02047* (2013.01); *G02B 6/03661* (2013.01); *G02B 6/03672* (2013.01)

(58) Field of Classification Search
CPC ............... G02B 6/024; G02B 6/02047; G02B 6/03672; G02B 6/03661; G02B 6/03688; G01N 2021/653
See application file for complete search history.

(56) References Cited

U.S. PATENT DOCUMENTS

| 7,889,960 B2 | 2/2011 | de Montmorillon et al. |
| 2006/0029344 A1* | 2/2006 | Farroni et al. ................. 385/123 |

(Continued)

FOREIGN PATENT DOCUMENTS

| KR | 10-2012-0046993 | 5/2012 |
| WO | WO 2010044510 A1 * | 4/2010 |

(Continued)

OTHER PUBLICATIONS

Nakstad et al., "Oil and Gas Application, Probing Oil Fields", Nature Photonics, Mar. 2008, pp. 147-149, vol. 2, Nature Publishing Group, Norway.
(Continued)

*Primary Examiner* — Charlie Y Peng
(74) *Attorney, Agent, or Firm* — Fasken Martineau DuMoulin (57) ABSTRACT

An optical fiber for use in a Coherent Anti-Stokes Raman Scattering (CARS) endoscope, comprising a core guiding lightwaves at a pump wavelength and at a Stokes wavelength, the core being single-mode at both wavelengths. The core is surrounded by cladding layers, including an inner cladding layer, a trench cladding layer, an intermediate cladding layer and an outer cladding layer. The refractive index of the trench cladding layer is lower than those of both neighboring cladding layers so as to define a trench in the radial refractive-index profile. The bending losses of the fundamental $LP_{01}$ mode of the fiber at the Stokes wavelength are limited while maintaining high confinement losses for the higher-order $LP_{11}$ mode of the fiber at the pump wavelength. The combination of the intermediate and outer cladding layers forms a multimode waveguide for guiding a collected CARS signal generated by an object or medium probed with the endoscope.

4 Claims, 10 Drawing Sheets

(51) Int. Cl.
*G02B 6/02* (2006.01)
*G02B 6/036* (2006.01)

(56) References Cited

U.S. PATENT DOCUMENTS

2008/0317418 A1* 12/2008 Taniguchi et al. ............ 385/122
2012/0010513 A1* 1/2012 Wong et al. .................. 600/476

FOREIGN PATENT DOCUMENTS

WO  WO 2011140657 A1 * 11/2011
WO  2012/060563 A2  5/2012

OTHER PUBLICATIONS

Kato et al., "Dispersion flattened transmission line consisting of wide-ban non-zero dispersion shifted fiber and dispersion compensating fiber module", Optical Fiber Technology, May 2002, pp. 231-239, vol. 8, Academic Press, USA.

Li et al., "Optical Fiber Design for Field Mountable Connectors", Journal of Lightwave Technology, Mar. 2000, pp. 314-319, vol. 18, No. 3, IEEE, USA.

Veilleux et al., Design and modeling of a prototype fiber scanning CARS endoscope, Endoscopic Microscopy V, 12 pages, vol. 7558, Proc. of SPIE, Downloaded from: http://proceedings.spiedigitallibrary.org/ on Jan. 28, 2013.

Ghandehari et al., "Near-Infrared Spectroscopy for In Situ Monitoring of Geoenvironment", Journal of Geotechnical and Geoenvironmental Engineering, Apr. 2008, pp. 487-496, vol. 134, No. 4, ASCE, USA.

* cited by examiner

OPTICAL FIBER FOR COHERENT ANTI-STOKES RAMAN SCATTERING ENDOSCOPES

TECHNICAL FIELD

The invention relates to an optical fiber and, more particularly, to an optical fiber suitable for use in a Coherent Anti-Stokes Raman Scattering (CARS) endoscope.

BACKGROUND OF THE ART

Optical probes with small footprints are employed in applications where interrogating materials and media with conventional means become difficult because of restricted access and/or environmental hazards. For example, such optical probes can be utilized for probing oil fields (see Nakstad et al., "Probing oil fields", Industry Perspectives, Oil and Gas Applications, Technology Focus: Optical-fibre sensors, Nature Photonics Vol. 2, No. 3, pp. 147-149, (2008)), nuclear reactors (see PCT Pat. Appl. Pub. No. WO/2012060563 OPTICAL FIBER PROBE FOR MEASURING PH IN NUCLEAR REACTOR COOLING SYSTEM AND PH MEASURING SYSTEM USING SAME) or contaminated soils (see Ghandehari et al., "Near-Infrared Spectroscopy for In Situ Monitoring of Geoenvironment", JOURNAL OF GEOTECHNICAL AND GEOENVIRONMENTAL ENGINEERING Vol. 134, No. 4, pp. 487-496, (2008)). In the medical field, optical fiber endoscopes constitute tools of prime importance for clinicians, as internal organs and tracts can often be readily accessed without surgery for diagnostic and treatment purposes.

Optical probes can exploit various interaction mechanisms or principles involving light to extract information from the probed object or medium. For some types of probes, excitation photons impinge on the object and interact with it so that secondary photons are created within the object or at its surface. Several light-matter interaction mechanisms can lead to the generation of secondary photons, such as Raman scattering, harmonic generation and fluorescence, to name just a few.

Useful information about the chemical composition, function and structure of the probed object or medium can be extracted from these secondary photons, once collected by appropriate means. One such means can involve a device comprising one or several optical waveguides, such as an optical fiber, wherein the secondary photons are collected and transmitted to a detection system. In particular, a dual-clad fiber (DCF) offers a well-suited, compact solution as both excitation and secondary light can be transmitted by the same fiber. In this case, the excitation light and the collected secondary light travel in different waveguides that are part of the same optical fiber.

An example of optical fiber probe using a DCF has been described by Veilleux et al. (see Veilleux et al., "Design and modeling of a prototype fiber scanning CARS endoscope" Proc. SPIE Vol. 7558, paper no. 75580D, (2010)). This probe, an imaging endoscope exploiting coherent anti-Stokes Raman scattering (CARS), could find numerous medical applications. CARS involves parametric processes initiated with two optical excitation signals having different wavelengths, namely a "pump" lightwave and a "Stokes" lightwave. A well-known limitation of CARS endoscopy comes from the generation of a contaminating background signal at the same wavelength as that of the CARS signal. The contaminating signal is generated through four-wave mixing (FWM) interactions involving the excitation photons as they propagate along the optical fiber. Appropriate means for managing this contaminating signal are desirable as otherwise part of it can be eventually collected and superposed to the CARS signal, thus leading to a degradation of the CARS signal-to-noise ratio (SNR). In the case of an imaging application, this contaminating background light limits the contrast of the images.

Various approaches have been proposed to mitigate this contaminating signal but, depending on the intended size of the overall probe, these approaches may not necessarily be practical. For example, the efficiency of the FWM nonlinear parametric process that gives rise to the contaminating signal at the CARS wavelength is polarization-dependent. The use of orthogonal polarizations for the pump and Stokes lightwaves can reduce the generation of the undesirable signal. The cross-polarization method implies that the polarization direction of one of the output lightwaves (either the pump or the Stokes) be rotated so that both lightwaves get co-polarized when incident on the probed tissue or object. The miniaturization of the probe may then become a challenge.

The use of a double-core fiber is another way to reduce the FWM generation. The pump and Stokes lightwaves propagate in two separate cores with a minimum of overlap between the corresponding transverse modes. However, the double-core design has its own limitations: the injection of the pump and Stokes lightwaves into separate cores gets more complex and the lens design at the output end of the fiber must ensure good spatial overlap of the light beams on the tissue under examination, thus resulting in additional constraints to account for in the course of the design phase.

SUMMARY

In accordance with one broad aspect of the present invention, there is provided an optical fiber for use in a Coherent Anti-Stokes Raman Scattering (CARS) endoscope. The optical fiber comprises a core guiding lightwaves at a pump wavelength and at a Stokes wavelength, the core being single-mode at both wavelengths. The core is surrounded by cladding layers, including an inner cladding layer, a trench cladding layer, an intermediate cladding layer and an outer cladding layer. The refractive index of the trench cladding layer is lower than those of both neighboring cladding layers so as to define a trench in the radial refractive-index profile. The bending losses of the fundamental $LP_{01}$ mode of the fiber at the Stokes wavelength are limited while maintaining high confinement losses for the higher-order $LP_{11}$ mode of the fiber at the pump wavelength. The combination of the intermediate and outer cladding layers forms a multimode waveguide for guiding a collected CARS signal generated by an object or medium probed with the endoscope.

In accordance with another broad aspect, there is provided an optical fiber for use in a CARS endoscope. The fiber comprises a core that guides lightwaves at a pump wavelength and at a Stokes wavelength, the core being single-mode at both wavelengths while having a radius $a_1$ and a refractive index $n_1$. The optical fiber also comprises, successively, an inner cladding layer having a refractive index $n_2$ lower than the refractive index $n_1$ ($\delta n_1 = n_1 - n_2 > 0$), a trench cladding layer having an inner radius $a_2$ and a refractive index $n_3$ lower than the refractive index $n_2$, an intermediate cladding layer having a refractive index $n_4$ higher than the refractive index $n_3$, and an outer cladding layer having a refractive index $n_5$, the refractive index $n_5$ being lower than the refractive index $n_4$. The intermediate cladding layer encloses two stress-applying parts to maintain the polarization direction of the lightwaves propagating in the fiber. More particularly, the width W and depth $\delta n_2$ ($\delta n_2 = n_4 - n_3$) of the trench cladding layer are selected to limit the bending losses of the fundamental $LP_{01}$ mode of the fiber at the Stokes wavelength while maintaining high confinement losses for the higher-order $LP_{11}$ mode of the fiber at the pump wavelength. In addition, the combination of the intermediate and outer cladding layers is adapted to form a multimode optical waveguide for guiding a lightwave at a CARS wavelength, this lightwave resulting from the part of the CARS signal generated in a probed object or medium that is collected by the distal end of the CARS endoscope.

In accordance with still another aspect, there is provided an optical fiber for use in a Coherent Anti-Stokes Raman Scattering (CARS) endoscope. The optical fiber comprising: a core having a radius $a_1$ and a refractive index $n_1$, the core extending along a longitudinal axis, the core being adapted to guide a Stokes lightwave at a Stokes wavelength and a pump lightwave at a pump wavelength along a first propagation direction parallel to the longitudinal axis, said core being single-mode at the Stokes and pump wavelengths, each of the Stokes lightwave and the pump lightwave having a direction of polarization; an inner cladding layer surrounding the core, the inner cladding layer having a refractive index $n_2$, the refractive index $n_1$ being higher than the refractive index $n_2$, the refractive index $n_1$ and the refractive index $n_2$ being chosen to obtain a predetermined value of the numerical aperture of the core; a trench cladding layer surrounding the inner cladding layer and having a trench inner radius $a_2$, a width W, and a refractive index $n_3$, the refractive index $n_3$ being lower than the refractive index $n_2$; an intermediate cladding layer surrounding the trench cladding layer and having a refractive index $n_4$, the refractive index $n_4$ being higher than the refractive index $n_3$ by a depth $\delta n_2$ equal to a difference $n_4 - n_3$; two stress-applying parts enclosed within the intermediate cladding layer and disposed symmetrically on either side of the longitudinal axis, each stress-applying part being disposed substantially parallel to the longitudinal axis, the stress-applying parts being adapted to maintain the direction of polarization of the pump lightwave and of the Stokes lightwave; and an outer cladding layer surrounding the intermediate cladding layer and having a refractive index $n_5$, the refractive index $n_5$ being lower than the refractive index $n_4$ allowing said optical fiber to act as a multimode waveguide for guiding a CARS lightwave at a CARS wavelength along a second propagation direction parallel to the longitudinal axis and opposite to the first propagation direction.

In one embodiment, the width W and depth $\delta n_2$ are selected to limit bending losses of a fundamental $LP_{01}$ mode of the optical fiber at the Stokes wavelength below 0.5 dB/turn for a fiber curved with a radius of about 2 cm while maintaining confinement losses above 5 dB/m for a higher-order $LP_{11}$ mode of the optical fiber at the pump wavelength.

In one embodiment, the Stokes wavelength is about 1064 nm and the pump wavelength is about 816 nm.

In one embodiment, the trench cladding layer has a width W between 3 and 5 µm.

In one embodiment, the trench cladding layer has a depth $\delta n_2$ between $3.0 \times 10^{-3}$ and $5.0 \times 10^{-3}$.

In one embodiment, the optical fiber has a nominal mode field diameter (MFD) between 9 and 11 µm at 1064 nm and between 7 and 9 µm at 816 nm.

In one embodiment, the confinement losses of the higher-order modes are at least 5 dB/m at the pump wavelength.

In one embodiment, the bending losses of the $LP_{01}$ fundamental mode at the Stokes wavelength are less than 0.5 dB/turn for a fiber curved with a radius of 2 cm.

In one embodiment, the core radius $a_1$ is between 3 and 4 µm.

In one embodiment, the trench inner radius $a_2$ is between 9 and 15 µm.

In one embodiment, the refractive indices $n_1$ and $n_2$ are such that the numerical aperture of the fiber, defined as NA= $\sqrt{n_1^2 - n_2^2}$ is between 0.07 and 0.12.

In one embodiment, the intermediate cladding layer is made out of pure fused silica.

In another embodiment, the intermediate cladding layer is made out of doped silica, such as Germanium- or Fluorine-doped silica.

In one embodiment, the trench cladding layer is made out of doped silica, such as Fluorine-doped silica.

In one embodiment, the stress-applying parts (SAPs) are made out of doped silica, such as Boron-doped silica.

In one embodiment, the outer cladding layer is made out of doped silica, such as Fluorine-doped silica.

In another embodiment, the outer cladding layer is made out of a low-index polymer.

BRIEF DESCRIPTION OF THE DRAWINGS

Having thus generally described the nature of the invention, reference will now be made to the accompanying drawings, showing by way of illustration example embodiments thereof and in which:

FIG. 1 (prior art) includes FIG. 1A and FIG. 1B in which FIG. 1A illustrates an example index profile of a prior art step-index fiber of common use in CARS applications, while

FIG. 2 includes FIG. 2A, FIG. 2B and FIG. 2C in which FIGS. 2B and 2C show the corresponding refractive-index profile along the X and Y axes, respectively, shown in FIG. 2A;

FIG. 3 includes FIG. 3A and FIG. 3B in which

FIG. 4 includes FIG. 4A, FIG. 4B, FIG. 4C and FIG. 4D in which

FIG. 6 includes FIG. 6A and FIG. 6B which show the radial refractive index profiles measured along two orthogonal transverse axes of a fabricated optical fiber.

DETAILED DESCRIPTION

The peak intensities of the lightwaves propagating in the single-mode core of the optical fiber can be reduced by designing the radial refractive-index profile of the fiber so that it leads to enlarged mode areas at the wavelengths of the lightwaves. To ensure similar optical intensities incident on the tissue probed using a CARS endoscope, the lens design at the distal end of the optical fiber needs to be modified in a relatively simple manner as compared to the case where a more common fiber is used in the endoscope.

According to its nonlinear character, FWM is an intensity-dependent process. This means that any attempt at spreading the optical powers carried by the pump and Stokes lightwaves on larger mode areas would reduce the peak intensity of each lightwave for a same injected power, the lower optical intensities thus resulting in a lower efficiency of the FWM process. The mode areas of the lightwaves can be increased by enlarging the core of the fiber and/or by reducing its numerical aperture.

The core of the fiber is single-mode at the two wavelengths of interest and the fiber design should take two conflicting requirements into account: 1) the bending losses of the fundamental mode at the longer Stokes wavelength should remain low at the smallest bending radius of the fiber (for example below 0.2 dB for half-a-turn at a 2 cm bending radius), and: 2) the confinement losses of the higher-order modes should be high enough (for example above 5 dB/m) so as to filter them out within at most a few meters of fiber to remain effectively single-mode at the shorter pump wavelength. These two requirements conflict with one another as the first one implies a core that sufficiently guides the fundamental modes at both wavelengths, whereas the second one would be easier to fulfill with a less guiding core.

Figure 1A:
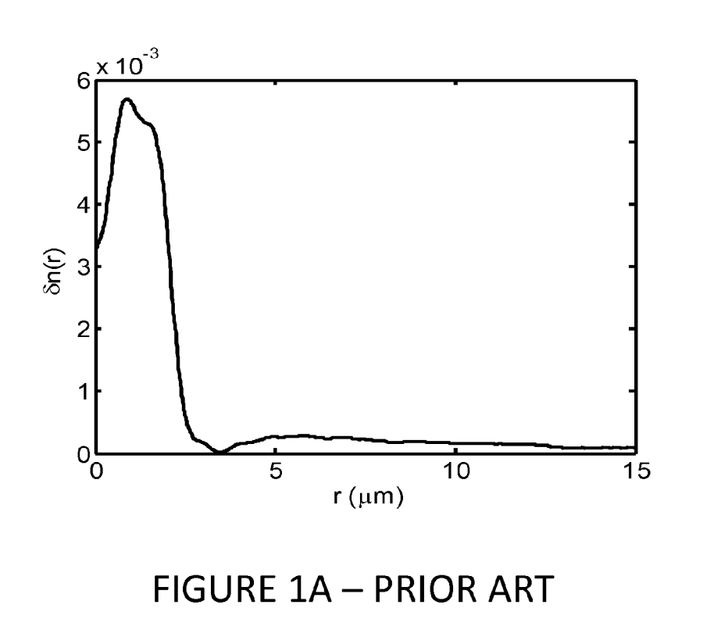
Figure 1B:
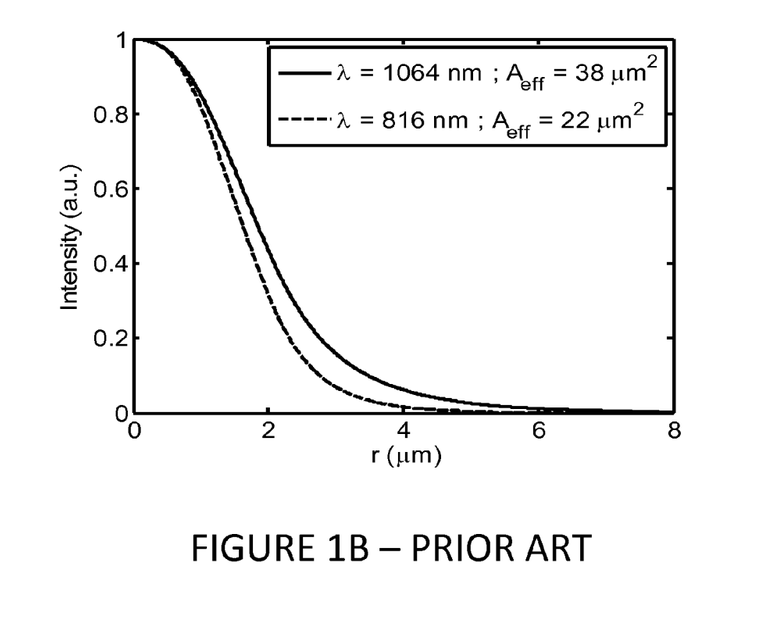
FIG. 1B depicts the corresponding fundamental mode profiles at two different wavelengths, the on-axis intensity being normalized to unity in both cases.

FIG. 1A depicts an example refractive-index profile of a prior art step-index fiber of common use in endoscopes intended for CARS applications. Example design parameters are a core diameter of ~5 μm and a numerical aperture NA of ~0.12. FIG. 1B depicts the corresponding fundamental mode profiles with their on-axis intensities normalized to unity. The label r in the horizontal axis of FIG. 1A and FIG. 1B denotes the radial position with respect to the longitudinal center axis of the fiber. The corresponding effective mode areas of the depicted profiles are ~22 μm² at 816 nm wavelength and 38 μm² at 1064 nm wavelength.

Figure 2A:
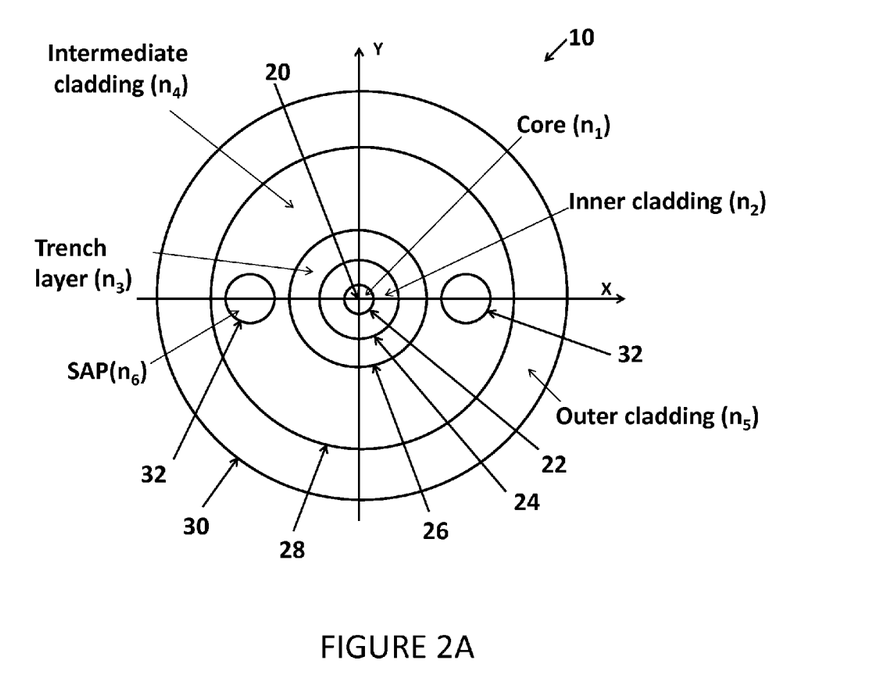
FIG. 2A is a schematic illustration of the structure of an embodiment of the optical fiber, which shows the presence of stress-applying parts (SAPs) that serve to maintain the polarization direction of the lightwaves propagating in the fiber.

The schematic illustration of FIG. 2A depicts the structural characteristics of a first embodiment of an optical fiber 10 that fulfills the various requirements mentioned earlier and intended for use in a CARS endoscope. Starting from the center position of the illustration, the optical fiber 10 first includes a core 22 that is single-mode for lightwaves at a pump wavelength and at a Stokes wavelength, the core 22 having a radius $a_1$ (not shown in FIG. 2A). The core 22 is made out of an optical material having a refractive index $n_1$ within a spectral region encompassing the wavelengths of interest. The core 22 is substantially centered on the longitudinal axis 20 of the fiber, which extends perpendicularly to the plane of FIG. 2A while being coincident with the intersection of the two orthogonal transverse axes labeled X and Y in FIG. 2A. The core 22 is surrounded by an inner cladding layer 24 having a refractive index $n_2$, this layer being in turn surrounded by a trench cladding layer 26 having an inner trench radius $a_2$ (not shown in FIG. 2A) and a refractive index $n_3$. The optical fiber 10 further includes an intermediate cladding layer 28 having a refractive index $n_4$ and that surrounds the trench cladding layer 26. The cladding structure of the fiber terminates with an outer cladding layer 30 having a refractive index $n_5$ and that surrounds the intermediate cladding layer 28.

As also shown in FIG. 2A, this first embodiment of the optical fiber 10 also includes two stress-applying parts (SAPs) 32 that are enclosed within the intermediate cladding layer 28. The SAPs 32 are disposed symmetrically on either side of the longitudinal axis 20, each SAP 32 being elongated substantially parallel to the longitudinal axis 20. As it is well known in the art, the SAPs 32 are included to maintain the polarization direction of the (polarized) light propagating in the fiber.

Figure 2B:
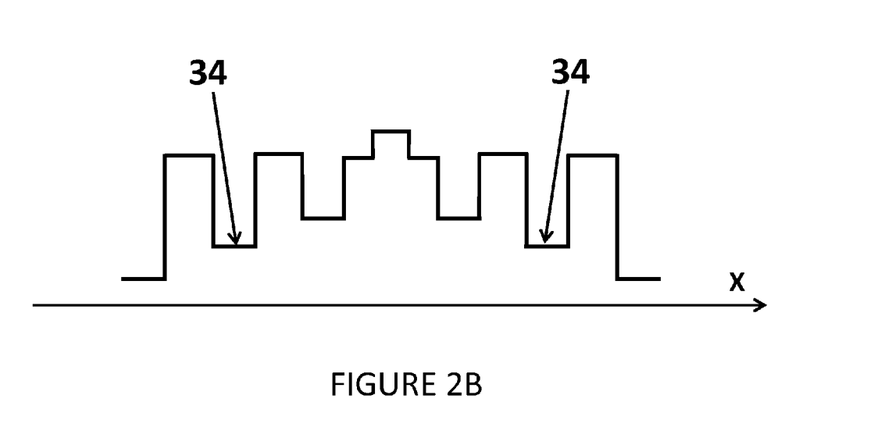
Figure 2C:
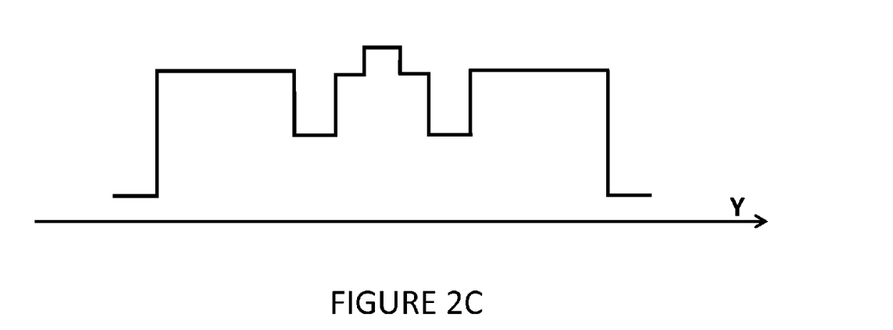

Examples of radial refractive-index profiles corresponding to the first embodiment of the optical fiber 10 depicted in FIG. 2A are shown in FIGS. 2B and 2C. The refractive-index profiles show the relative changes of the refractive index from cladding to cladding when moving along the X (FIG. 2B) and Y (FIG. 2C) axes. One can easily see that both profiles differ only by the presence of two regions 34 of lower refractive index in FIG. 2B and located symmetrically on either side of the center position. These regions 34 are signatures of both SAPs 32, which are shown as being disposed along the X axis in FIG. 2A.

Figure 3A:
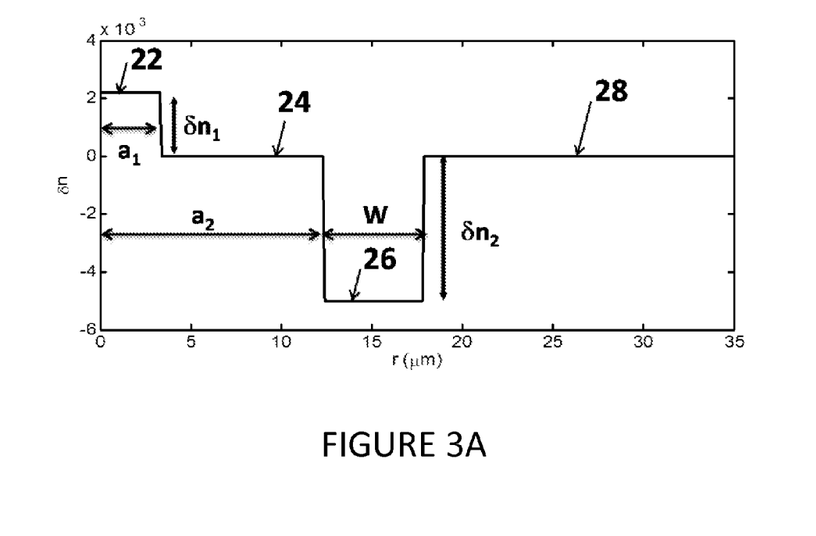
FIG. 3A shows an exemplary radial refractive-index profile according to an embodiment of the optical fiber, the corresponding fundamental mode profiles at two different wavelengths being illustrated in FIG. 3B.

The key features of an exemplary refractive-index profile for the first embodiment of the optical fiber 10 can be described by referring to FIG. 3A, which shows the evolution of the local refractive index over a limited interval of the radial position r, the interval starting at the longitudinal center axis 20 of the fiber 10. It is assumed here that the position r extends along a radius that does not intersect the SAPs 32, so that the effect of these elements on the radial refractive-index profile does not show up in FIG. 3A. In addition, in this specific example, the intermediate cladding layer 28 extends beyond the interval of radial positions selected for FIG. 3A, so that the refractive index $n_5$ of the outer cladding layer 30 is not shown in the figure. This choice is to better emphasize the evolution of the refractive index within the radial position interval covered by the innermost cladding layers.

The refractive index $n_1$ of the core 22 is higher than the refractive index $n_2$ of the inner cladding layer 24, the difference between both refractive indices being labeled as $\delta n_1 = n_1 - n_2$ in FIG. 3A. It will be understood by those skilled in the art that the refractive indices $n_1$ and $n_2$ dictates the value of the numerical aperture of the core 22, given by NA= $\sqrt{n_1^2 - n_2^2}$. For example, the refractive indices $n_1$ and $n_2$ in one embodiment of the optical fiber 10 can be chosen such that the numerical aperture of the core 22 is between 0.07 and 0.12. The core 22 has a radius $a_1$.

The trench cladding layer 26 has an inner trench radius $a_2$ and is added to the optical fiber 10 in order to fulfill requirements similar to those stated earlier, for example for limiting the bending losses of the fundamental $LP_{01}$ mode at the Stokes wavelength (typically below 0.2 dB for half-a-turn at a 2 cm bending radius) while maintaining sufficient confinement losses for the higher-order modes at the pump wavelength (typically above 5 dB/m). The trench cladding layer 26 stands out in the optical fiber 10 mainly by its refractive index $n_3$ that is selected lower than those of the neighboring inner 24 and intermediate 28 cladding layers. Two parameters are particularly useful for defining the impact of the trench cladding layer 26 on the optical waveguiding properties of the fiber 10, these parameters being the width W of this layer and the difference $\delta n_2 = n_4 - n_3$ between the refractive indices of the trench 26 and intermediate 28 cladding layers. The difference $\delta n_2$ is often referred to as the depth of the trench cladding layer 26. An important task in the design of the optical fiber 10 is the selection of the values of W and $\delta n_2$ required to fulfill the requirements relating to both bending and confinement losses at the wavelengths of interest. A compromise must be made in the design process: a wide trench cladding layer 26 is certainly beneficial for limiting the bending losses but this also comes with a reduction of the confinement losses of the $LP_{11}$ mode, that should be kept as large as possible.

Referring back to FIG. 3A, the refractive index $n_4$ of the intermediate cladding layer 28 can be chosen higher, lower or equal to the refractive index $n_2$ of the inner cladding layer 24. Both indices have the same value in the exemplary refractive-index profile depicted in FIG. 3A, although, in other embodiments, the indices can differ without departing from the scope of the invention.

Referring back to FIG. 2A, the refractive index $n_5$ of the outer cladding layer 30 is selected lower than that of the intermediate cladding layer 28, so that the whole optical fiber structure also acts as a multimode waveguide. Since the optical fiber 10 of the present embodiment is intended for use in a CARS endoscope, the optical waveguide discussed herein is particularly helpful for guiding a lightwave at the CARS wavelength. This lightwave results from the capture, at the distal end of the fiber, of a part of the CARS signal (also referred earlier to as the secondary photons) generated in the object or medium probed with the endoscope. It can be noted that the lightwave at the CARS wavelength guided by this multimode waveguide propagates in a direction opposite to that of both Stokes and pump lightwaves guided by the core 22 and that serve to optically excite the probed object. As one can see in the schematic illustration of FIG. 2A, the width (thickness) of the intermediate cladding layer 28 must be large enough at least to fit the SAPs 32 located therein. This means that the width of this layer must be larger than the diameter of each individual SAP 32. Furthermore, increasing the width of the intermediate cladding layer 28 favors the multimode character of the optical waveguide, thus increasing the optical collection efficiency of the CARS signal generated in the probed object. As also known in the art, the optical collection efficiency of the CARS signal can be further increased by disposing a set of multimode collection optical fibers around the periphery of a center optical fiber, thus forming a type of fiber bundle adapted for use in a CARS endoscope.

The optical fiber 10 of the present embodiment may have inner 24 and intermediate 28 cladding layers that are made out of pure fused silica, but these layers could also be made out of other suitable materials, such as doped silica. The intermediate cladding layer 28 can be made out of Germanium- or Fluorine-doped silica. Likewise, the trench cladding layer 26 can be made out of doped silica such as Fluorine-doped silica. The outer cladding layer 30 can be made out of silica glass doped with various materials such as Fluorine. Alternatively, the outer cladding layer 30 can be made out of a low-index polymer material. Finally, doped silica, such as Boron-doped silica, is a suitable optical material for the stress-applying parts 32.

Figure 3B:
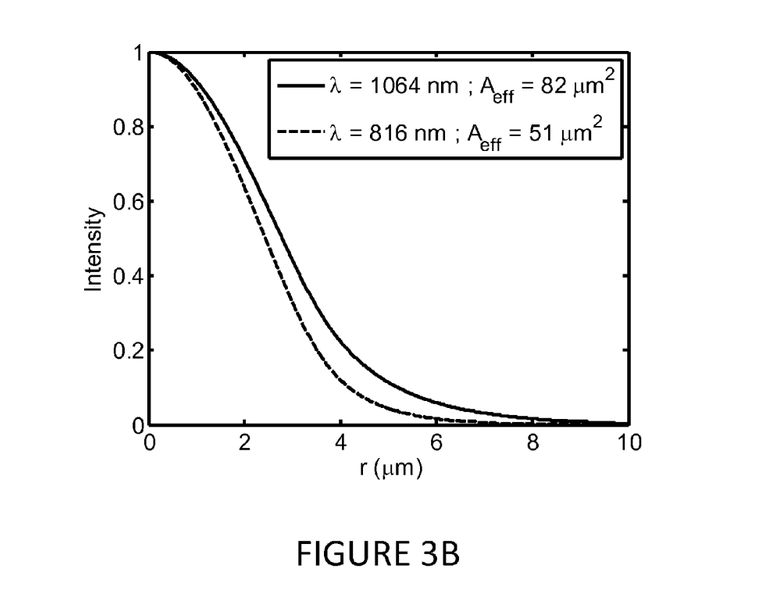

Exemplary values for the Stokes and pump wavelengths are 1064 nm and 816 nm, respectively. As it will be understood by those skilled in the art, optically exciting an object or medium with these exemplary wavelength values results in the generation of a CARS signal having a wavelength of about 662 nm. Among other things, selecting these Stokes and pump wavelengths offer the advantages of obtaining sizeable optical powers in a cost-effective fashion since affordable laser sources emitting at these wavelengths are readily available in the marketplace. Of course, other values for the Stokes and pump wavelengths can be selected without departing from the scope of the invention. FIG. 3B illustrates the fundamental mode profiles calculated for lightwaves at both 1064 nm and 816 nm wavelengths and propagating in an optical fiber 10 characterized by the radial refractive-index profile depicted in FIG. 3A. Example values for the effective mode areas are ~50 $\mu m^2$ at 816 nm and ~80 $\mu m^2$ at 1064 nm. The effective mode areas are therefore doubled when compared with those indicated in FIG. 1B and obtained using the prior-art refractive-index profile of FIG. 1A. This increase comes from a slightly larger core 22 (6.6 µm diameter) and a lower numerical aperture (NA=0.08).

The expected reduction in FWM generation implied by using an optical fiber 10 offering a higher effective mode area is estimated as follows. The optical intensity of the FWM signal $I_{FWM}$ is related to the pump and Stokes intensities $I_p$ and $I_S$, respectively, as $I_{FWM} \propto I_p^2 I_S$. Then, for identical input powers the reduction of $I_p$ and $I_S$ implied by the increased mode areas would suggest a reduction of about 10 dB in the peak optical intensity of the FWM signal.

In addition to the differences in the numerical aperture and diameter of the fiber core 22, the radial refractive-index profiles depicted in FIGS. 1A and 3A are distinguishable by the presence of a trench cladding layer 26 (i.e., an index depression) in the radial refractive-index profile of the optical fiber 10, as clearly illustrated in FIG. 3A. The relevant parameters for designing an optical fiber 10 according to the first embodiment are the numerical aperture NA and radius $a_1$ of the core 22, and the inner radius $a_2$, the width W and the depth $\delta n_2$ of the trench cladding layer 26.

As mentioned earlier, the numerical aperture and diameter of the core 22 in the exemplary refractive-index profile of the first embodiment illustrated in FIG. 3A were selected to be 0.08 and 6.6 µm, respectively, to obtain the fundamental mode profile shown in FIG. 3B. The effective mode field diameters ($MFD_{eff} = 2(A_{eff}/\pi)^{1/2}$) are about 8.0 µm at the pump wavelength of 816 nm and about 10.2 µm at the Stokes wavelength of 1064 nm. These results were obtained using a trench cladding layer 26 having an inner radius $a_2$ of 12.3 µm. The width W and depth $\delta n_2$ of the trench cladding layer 26 are thus the design parameters that remain to be optimized.

Figure 4A:
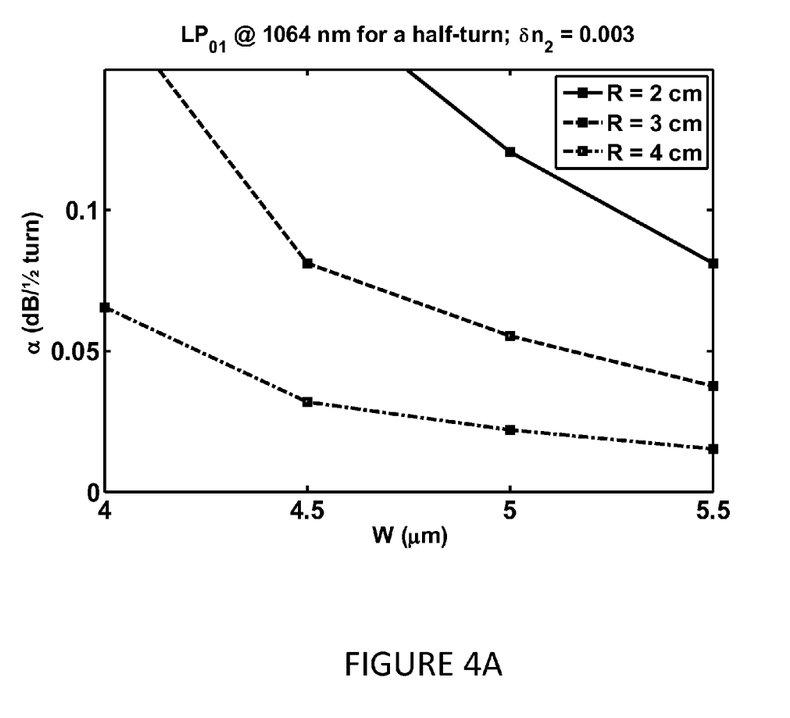
FIG. 4A, FIG. 4B and FIG. 4C depict the dependence of the bending losses of the $LP_{01}$ fundamental mode at 1064 nm wavelength on some of the design parameters (the width W and depth $\delta n_2$ of the trench cladding layer)
Figure 4B:
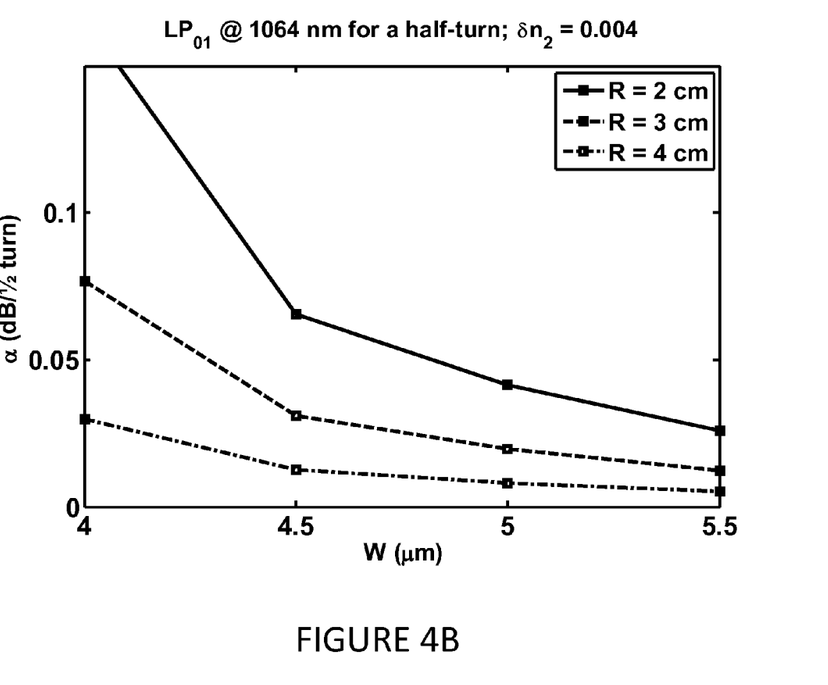
Figure 4C:
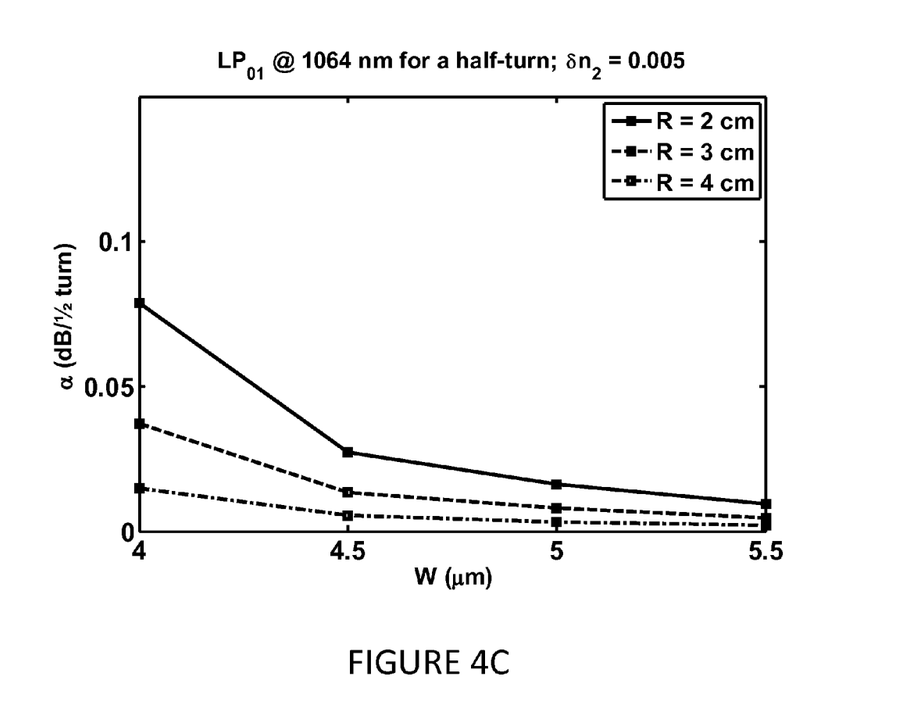
Figure 4D:
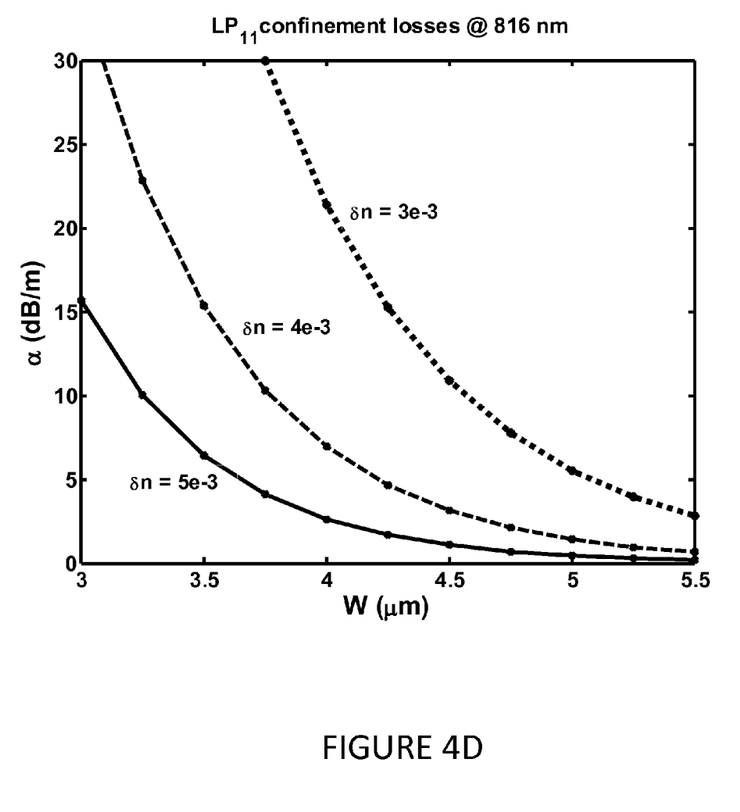
FIG. 4D shows how the confinement losses of the $LP_{11}$ mode at 816 nm wavelength depend on the same design parameters.

FIG. 4, including FIGS. 4A to 4D, illustrates design curves that show the effects of the width W and depth $\delta n_2$ of the trench cladding layer 26 on the waveguiding properties of the fiber 10. FIGS. 4A, 4B and 4C depict the dependence of the bending losses of the $LP_{01}$ fundamental mode at 1064 nm on some of the design parameters. The bending losses are generally lower at shorter wavelengths, so that the emphasis is put on the highest of the two wavelengths. The graphs of FIGS. 4A, 4B and 4C show the bending losses as functions of the trench width W for three different bending radii R of the optical fiber 10 and for three values of the trench depth $\delta n_2$. As mentioned above, the need to minimize the bending losses at the longer Stokes wavelength conflicts with the need to make the confinement losses of the $LP_{11}$ mode at the shorter pump wavelength as high as possible. The corresponding losses at the Stokes wavelength are necessarily higher. Similarly, higher-order modes suffer from still higher confinement losses than those of the $LP_{11}$ mode. FIG. 4D shows how these confinement losses at 816 nm depend on the same design parameters as the bending losses. The curves presented in FIG. 4 have been computed using a diameter of 6.6 µm and a numerical aperture of 0.08 for the core 22, while an inner radius $a_2$ of 12.3 µm was selected for the trench cladding layer 26.

An example of application of the design curves shown in FIGS. 4A to 4D can be worked out in the following way, starting from the refractive-index profile as depicted in FIG. 3A and wherein the trench cladding layer 26 has, for example, a width W of 4.5 µm. From the curves of FIG. 4D, one readily finds that the confinement losses of the $LP_{11}$ mode of the lightwave at the pump wavelength of 816 nm can be kept above 5 dB/m by selecting a trench cladding layer 26 characterized by a depth $\delta n_2$ lower than about 0.0037. The nominal value $\delta n_2 = 0.003$ is therefore suitable. FIG. 4A shows the evolution of the bending losses incurred by the fundamental mode at 1064 nm evaluated at this depth value of the trench cladding layer 26. The curves plotted in FIG. 4A show that the bending losses for half a turn of the fiber 10 attain about 0.12 dB when the radius of curvature of the fiber is 2 cm. As a result, the requirement of limiting the bending losses below 0.5 dB for a complete turn with a 2 cm bending radius is fulfilled when using a trench cladding layer 26 having a width of 4.5 µm and a depth $\delta n_2$ of 0.003.

Figure 5:
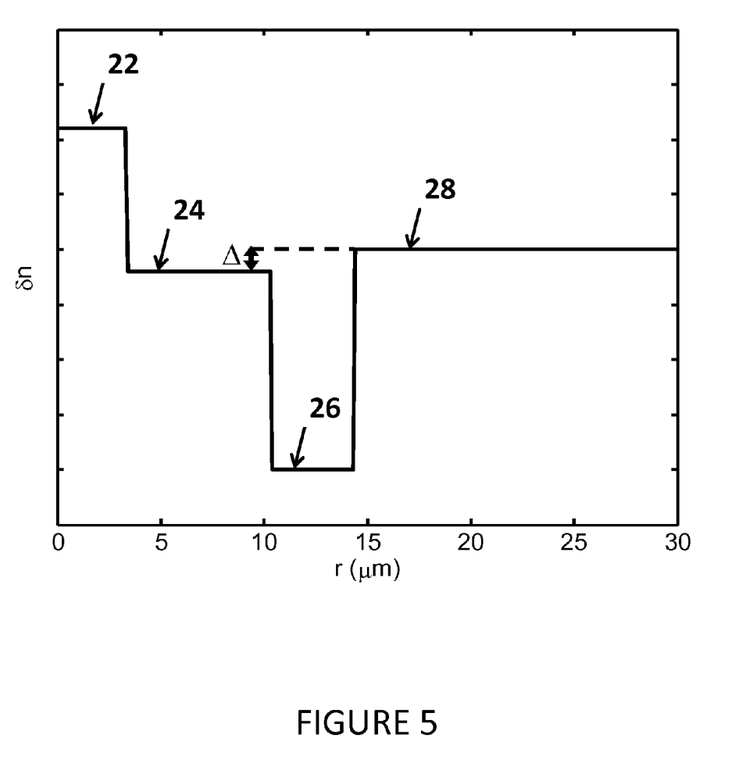
FIG. 5 illustrates an exemplary radial refractive-index profile according to another embodiment of the optical fiber, in which the refractive indices of the inner cladding layer and intermediate cladding layer differ by an amount $\Delta$.

FIG. 5 illustrates an exemplary refractive-index profile of a second embodiment of the optical fiber 10 in which the refractive index $n_4$ of the intermediate cladding layer 28 differs from that of the inner cladding layer $n_2$ by an amount $\Delta$. This adds a degree of freedom in the optimization of the fiber design.

Figure 6A:
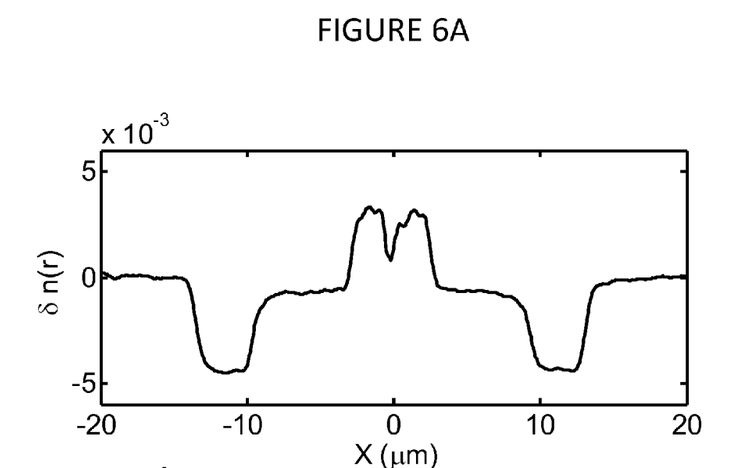
Figure 6B:
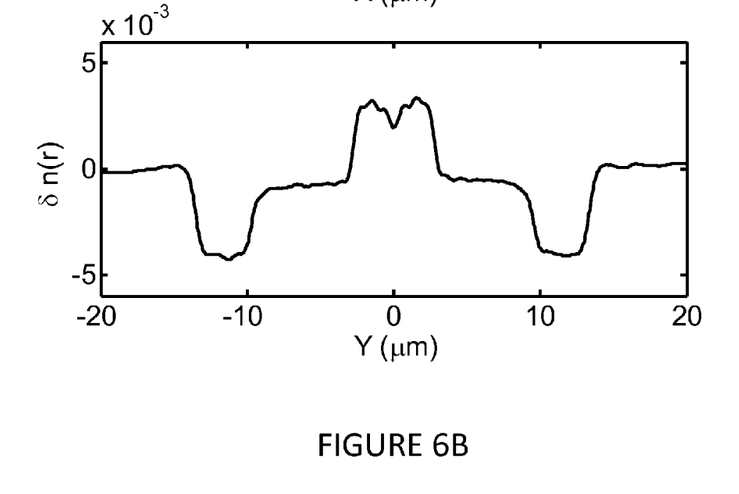

An optical fiber 10 having a radial refractive-index profile of the type corresponding to the first embodiment has been fabricated. The refractive-index profiles measured along two orthogonal axes X and Y transverse to the longitudinal center axis 20 of the fiber 10 are shown in FIG. 6. As it was the case in the schematic illustration of FIG. 2A, the X axis is parallel to the line that joins both SAPs 32 present in the fiber. Note that the refractive-index changes due to the presence of both SAPs 32 are not visible in FIG. 6A since the SAPs 32 are located beyond the limits of the horizontal axis of the graph.

Those skilled in the art of optical fiber design will recognize that the radial refractive-index profiles shown in FIGS. 3A, 5 and 6 are only examples intended to illustrate some embodiments, so that they should not be construed as limiting the scope of the invention. For instance, the radius $a_1$ of the core 22 can be selected between 3 µm and 4 µm. Accordingly, the inner radius $a_2$ of the trench cladding layer 26 can be between 9 µm and 15 gm while this cladding layer can have a width W selected in the range from 3 µm to 5 µm and a depth $\delta n_2$ ranging from $3.0 \times 10^{-3}$ to $5.0 \times 10^{-3}$. In the case where the Stokes and pump wavelengths are about 1064 nm and 816 nm, respectively, the optical fiber 10 can have a nominal mode field diameter (MFD) between 9 µm and 11 µm at 1064 nm and between 7 µm and 9 µm at 816 nm. It is possible to add extra features, for example a ring section having a raised refractive index and which is located beyond the trench cladding layer 26. This ring could help in increasing the confinement losses of the $LP_{11}$ mode. Finally, the design curves plotted in the graphs of FIGS. 4A to 4D can be computed for other pairs of Stokes and pump wavelengths and then used as a basis for the design of optical fibers 10 suitable for CARS endoscopes operating with a desired excitation wavelength pair.

The embodiments described above are intended to be exemplary only. The scope of the invention is therefore intended to be limited solely by the appended claims.

We claim:

1. An optical fiber for use in a Coherent Anti-Stokes Raman Scattering (CARS) endoscope, the optical fiber comprising:
   a core having a radius $a_1$ and a refractive index $n_1$, the core extending along a longitudinal axis, the core being adapted to guide a lightwave at a Stokes wavelength and a lightwave at a pump wavelength along a first propagation direction parallel to the longitudinal axis, said core being single-mode at the Stokes and pump wavelengths, each of the lightwaves at the Stokes and pump wavelengths having a direction of polarization;
   an inner cladding layer surrounding the core, the inner cladding layer having a refractive index $n_2$, the refractive index $n_1$ being higher than the refractive index $n_2$, the refractive index $n_1$ and the refractive index $n_2$ being chosen to obtain a predetermined value of the numerical aperture of the core;
   a trench cladding layer surrounding the inner cladding layer and having a trench inner radius $a_2$, a width W, and a refractive index $n_3$, the refractive index $n_3$ being lower than the refractive index $n_2$ of the inner cladding layer;
   an intermediate cladding layer surrounding the trench cladding layer and having a refractive index $n_4$, the refractive index $n_4$ being higher than the refractive index $n_3$ of the trench cladding layer by a depth $\delta n_2$ equal to a difference $n_4 - n_3$;
   two stress-applying parts enclosed within the intermediate cladding layer and disposed symmetrically on either side of the longitudinal axis, each stress-applying part being disposed substantially parallel to the longitudinal axis, the stress-applying parts maintaining the directions of polarization of the lightwaves at the Stokes and pump wavelengths as the lightwaves are guided within the core;
   an outer cladding layer surrounding the intermediate cladding layer and having a refractive index $n_5$, the refractive index $n_5$ being lower than the refractive index $n_4$ of the intermediate cladding layer;
   wherein a combination of the intermediate and outer cladding layers is adapted to allow the optical fiber to act as a multimode optical waveguide for guiding a lightwave at a CARS wavelength along a second propagation direction parallel to the longitudinal axis and opposite to the first propagation direction; and
   wherein the width W and depth $\delta n_2$ of the trench cladding layer are selected to limit bending losses of a fundamental $LP_{01}$ mode of the optical fiber at the Stokes wavelength below 0.5 dB/turn for a fiber curved with a radius of about 2 cm while maintaining confinement losses above 5 dB/m for a higher-order $LP_{11}$ mode of the optical fiber at the pump wavelength.

2. The optical fiber as claimed in claim 1, wherein the Stokes wavelength is about 1064 nm and the pump wavelength is about 816 nm.

3. The optical fiber as claimed in claim 2, wherein the optical fiber has a mode field diameter between 9 µm and 11 µm at the Stokes wavelength and between 7 µm and 9 µm at the pump wavelength.

4. The optical fiber as claimed in claim 1, wherein the trench cladding layer has a width W between 3 µm and 5 µm and a depth $\delta n_2$ between $3.0 \times 10^{-3}$ and $5.0 \times 10^{-3}$.

* * * * *